(12) United States Patent
van der Zel (10) Patent No.: US 8,828,287 B2
(45) Date of Patent: Sep. 9, 2014

(54) VENEERED DENTAL RESTORATION WITH A CONTROLLED SHADE

(75) Inventor: Joseph Maria van der Zel, Hoorn (NL)

(73) Assignee: Oratio B.V., Hoorn (NL)

(*) Notice: Subject to any disclaimer, the term of this patent is extended or adjusted under 35 U.S.C. 154(b) by 21 days.

(21) Appl. No.: 13/258,692

(22) PCT Filed: Mar. 25, 2009

(86) PCT No.: PCT/NL2009/050143
§ 371 (c)(1),
(2), (4) Date: Nov. 2, 2011

(87) PCT Pub. No.: WO2010/110650
PCT Pub. Date: Sep. 30, 2010

(65) Prior Publication Data
US 2012/0139142 A1    Jun. 7, 2012

(51) Int. Cl.
*A61C 13/08*    (2006.01)
(52) U.S. Cl.
USPC .......................................................... 264/20
(58) Field of Classification Search
CPC ................................................. A61C 13/0004
USPC .......................................................... 264/20
See application file for complete search history.

(56) References Cited

U.S. PATENT DOCUMENTS

| 4,433,959 A | 2/1984 | Faunce |
| 5,342,201 A * | 8/1994 | Oden ............................ 433/223 |
| 6,354,836 B1 | 3/2002 | Panzera |
| 7,086,863 B2 * | 8/2006 | Van der Zel .................... 264/20 |
| 7,162,321 B2 * | 1/2007 | Luthardt et al. ................ 264/16 |

FOREIGN PATENT DOCUMENTS

| EP | 0022655 | 1/1981 |
| EP | 0580565 | 1/1994 |
| EP | 0796596 | 9/1997 |
| EP | 1992302 | 11/2008 |
| WO | 0141670 | 6/2001 |

OTHER PUBLICATIONS

International Search Report dated Dec. 8, 2009, in corresponding PCT application.
Beuer F, Schweiger J, Eichberger M, Kappert HF, Gernet W, Edelhoff D., "High-strength CAD/CAM-fabricated veneering material sintered to zirconia copings—a new fabrication mode for all-ceramic restorations", Dent Mater. Jan. 2009;25(1):121-8.

* cited by examiner

*Primary Examiner* — Alison Hindenlang
(74) *Attorney, Agent, or Firm* — Young & Thompson

(57) ABSTRACT

Method for the manufacturing of a dental restoration including a dental restoration core 2 and a veneer layer 3, the veneer layer 3 being located at predetermined locations on the dental restoration core 2 and having predetermined thickness at the predetermined locations; the method including: manufacturing the dental restoration core; filling a void 5 in a mould block 1; 10 with a slurry or paste containing a constituent material for a veneer layer, the dental restoration core being positioned in the void; pressing the slurry or paste into the void, the void being arranged to have the slurry cover the dental restoration core at at least the predetermined locations; heating the slurry or paste in a hardening or pre-sintering process to obtain a hardened veneer structure covering the dental restoration core; milling a contour of the veneer layer into the hardened veneer structure to form the dental restoration.

16 Claims, 8 Drawing Sheets

Fig 1

101 — Optical scanning in the mouth of patient of scan model

102 — Optical scanning of gypsum model

103 — Design of restoration

104 — Identify shade

105 — Transfer in layers

106 — Design of crown layer build-up

107 — Production proces

VENEERED DENTAL RESTORATION WITH A CONTROLLED SHADE

FIELD OF THE INVENTION

The present invention relates to a method for manufacturing of a dental restoration comprising a dental restoration core and a veneer layer. Also, the invention relates to a dental restoration comprising a dental restoration core and a veneer layer. Moreover, the present invention relates to a computer system and a computer program for use according to the method of the present invention. Furthermore, the present invention relates to a shade guide of a series of dental elements or tooth samples

BACKGROUND

One of the blessings of computerized dentistry (CAD/CAM technologies) is that it enabled automated production of dental restoration structures of zirconia or metal alloy without intervention of a dental technician. The introduction of zirconia (zirconium-oxide) in restorative and prosthetic dentistry is most likely the decisive step towards the use of full ceramics without limitation. With the exception of zirconia, existing ceramics systems lack reliable potential for various indications for bridges without size limitations. Zirconia with its high strength and comparatively higher fracture toughness seems to buck this trend. With a three-point bending strength exceeding nine hundred mega Pascal (900 MPa), zirconia can be used in virtually every full ceramic prosthetic solution, including crowns, bridges, abutments and implant supra structures.

However, so far computerized dentistry could not provide the automatic production of structures of zirconia or metal alloy with one or more veneer layers without the intervention of a dental technician. A massive material without a veneer layer can never fulfill the aesthetic requirements of natural layered tooth. Surprisingly a method was found whereby both an automated manufacturing and an aesthetically pleasing result could be obtained.

Dental restorative systems that comprise a structural support part (a dental restoration core) and a visible part (e.g., a veneer layer) which is supported by the structural support part, seek to provide cosmetic and functional replacements for missing teeth.

A customized dental restoration should match the size, shape and contour of the original teeth in order to provide the best possible appearance. Standard methods for preparing dental restorative systems require considerable time, labor, and expense. Methods typically require that a patient makes between six and ten visits to the dentist's office to complete installation of the restorative system.

In the conventional method for the construction of a dental superstructure such as the dental restoration system, a physical model of the patient's gums and dental implant heads is prepared on which the dental superstructure is built manually using molding and other techniques known in the art. The craftsman or technician skilled at manufacturing such dental superstructures takes into consideration the size and shape of the desired dentures to be placed over the superstructure when crafting the same.

Conventionally a cast, milled or 3D free form printed core structure is veneered by the dental technician by hand using a time consuming layering technique.

Another possible production method is using CAD/CAM methods to produce a core structure by milling or 3D printing and the veneer in the form of a incinerable material such as methacrylate or polyurethane. The acrylic veneer is placed over the core, sprue channels attached and the assembly invested in a refractory investment material. By burnout of the incinerable part a veneer void is created. Next, the veneer void is replaced by hot pressing a glass ceramic above its melting temperature in the veneer void. The restoration is divested and further finished by cutting back and adding new porcelain and staining and glazing by the dental technician. Recently, another method to veneer a zirconia substructure was proposed for the production of a individual veneer cap of a glass ceramic (e.g., lithium silicate strengthened ceramic) which can be placed over the zirconia structure and whereby the veneer cap can be connected to the zirconia core structure by a low-fusing glass ceramic layer. (Beuer F, Schweiger J, Eichberger M, Kappert H F, Gernet W, Edelhoff D., "High-strength CAD/CAM-fabricated veneering material sintered to zirconia copings—a new fabrication mode for all-ceramic restorations", Dent Mater. 2009 January; 25(1):121-8).

Both methods still require manual steps in the production of the veneered restoration, while the manual steps in the present invention are limited to final glazing and staining of the restoration by the dental technician. Also they make use of massive materials that can never provide the same aesthetics as a multi-layered build-up.

The dental profession utilizes standardized shade guides. A well-known shade guide is the Vita™ Shade Guide, which includes sixteen different shades. However, these shade guides are utilized in a rudimentary fashion. The guide itself is a plastic plate with a plurality of removable color tabs that are shaped like a tooth e.g., a front tooth. Typically, to assess a patient's tooth shade, a dentist removes one of the colored tabs from the plate and holds it up to the patient's tooth so that he/she can visually determine the closest match possible. There is a necessity to improve color determination and simplify the handling of components for dental restorations. All major shade guides are derived from prosthesis teeth and are never meant for individual color determination of natural dentition. Color groups have been created but basically in human dentition only two color groups exist, reddish and yellowish. All deviated colors are caused by a colored transparency. Looking at the known Vita Shade Guide, only the reddish A and yellowish B group are in general, useful in determining human teeth. Shades in the C and D groups can be useful, but are only transparency variables of the A and B group. The downside of the A and B group is its inharmonious and irregular color gradient. Each color in the group has its own pigmentation and therefore a real fluent gradient is not present.

Understandably, there are many variables to this method, some of which stem from the subjectivity of the dentist making the eyeball assessment. Such shade guides have been utilized for decades and the color determination is made subjectively by the dentist.

In order to lower the subjective uncertainty a shade analyzer can be used that provides a methodology for assessing and communicating a patient's tooth color in an objective way.

The task of replacing a tooth is conventionally made of two separate steps. The first step is to measure the shape and color shade of a tooth to be replaced and the second step is to make a duplicate of that tooth according to the measurements taken in the first step.

In the first step, while the shape information can be acquired with molding technique, the measurement of the color shade and translucency of the tooth proves to be more challenging.

The quality of the dental prosthesis cannot be better than the data that serves to model the tooth. The precision of that model depends on several factors, like the quality of the illumination, the data acquisition by measuring and the processing of those data. The oldest and simplest way of determining the color shade of an object like a tooth is to compare visually the object with a chart of color shades. The results obtained with that method are however not very good because of the subjectivity of the human eye. Furthermore, the illumination of the tooth and of the chart may cause inappropriate color shade choices.

A quantitative method can be used to obtain a minimum of precision and of reproducibility in the measurement of the color shade of an object. Such quantitative methods can be classified by the type of illumination used, the measurement technique, the data processing and the comparison between the finished product and the original object.

The illumination is usually done by using fiber optics or a fiber optic bundle to illuminate the surface of the object to be measured. It is advantageous to control the illumination of the object since the characteristics of the illumination method may be taken into account during the data processing. Diffuse light provides a simple means to control illumination.

Several methods are known and used to convert the spectral decomposition or the data collected from a selected area into a single measurement that corresponds to the color perception of the human eye. The objective is to quantize the data and also to correct them as to be able to recreate the proper colors of the original model as the human eye perceives them. It is also important to be able to quantize the translucency of the materials.

In WO 97/01308 an oral camera connected to a shade analyzer subsystem, e.g. a digital video processor, and a color display monitor. The camera captures a digital color image of the patient's tooth and the subsystem compares that image to a stored plurality of tooth shades. Each tooth shade is represented in a block of data, including color image data, a tooth shade digital word, and a manufacturer type. The patient's tooth image includes an RBG chromatically representation that is scanned and compared with the several tooth shades stored in memory, and a match is determined and communicated to a user of the system. The methodology includes the specification of fractional tooth shades, if needed, corresponding to a plurality of glass ceramic forms for manufacturing a reconstructed tooth.

The information is then used by a technician to layer the crown following the identified color shade as measured and presented by the digital device. This process of fabricating a crown by a way of layering the material by hand is fairly tedious and costly as it takes much hands-on time. The result of this hand-work is unpredictable and the result depends to a large extent on the skills of the dental technician.

In EP 0796596 a system for recording the form and shade structure of teeth is described. The system is applied in the preparation and the production of ceramic or acrylic veneered restorations. The system consists of different assortments containing the models and images as well as layering schemes of different tooth form and shade structures. At the patient a comparison is made between the form and shade of the patients' teeth with the models, whereby the best fitting assortment is selected and in the dental laboratory according to the accompanying layering schemes nature-like restorations can be reproduced.

Because results of the digital color analyzer only result in prosthesis through the manual labor of the dental technician, still pseudo trial and error methods are used in the manufacturing of the prosthesis remain, with the result that prosthesis may need to be remade, leading to increased costs and inconvenience to the patient, dental professional and dental laboratory.

The main difficulty of measuring translucency and color simultaneously arises from the fact that the information of these two appearance factors is usually interlinked. Different approaches can be used to disambiguate these two appearance factors:

1. The auto-correlation functions for the three color channels provide information on the blur which can be caused by the translucency. Structured lighting can be used to increase and further disambiguate the signal.

2. Translucency can be evidenced by comparing successive images taken with alternately a white and a black background. A structured background can also be used to evidence transparency.

3. The knowledge of the color space covered by the material can also be used to parse color and translucency variations.

In most of the present existing CAD/CAM-systems dental restorations are produced from massive material blocks in the dental laboratory or in the dental practice. Machining a restoration from a uniformly colored monolithic block of material can never fulfill both the aesthetic demands and the requirements for strength.

It is an object of the present invention to provide a method for manufacturing an dental restoration. This object is achieved by a method according to claim 1.

Advantageously, the method provides the manufacture of a dental restoration in which the veneer layer is shaped on the dental restoration core without the need to define the veneer layer as a solid element before positioning on the dental restoration core. Application of a slurry or paste on the dental restoration core structure by using a mould block that has an open space that has the shape of the contour of the veneer layer surrounding the dental restoration, allows the direct formation of the veneer layer on the dental restoration core. The invention reduces the labor for layering the veneer on the dental restoration core.

It is also an object of the present invention to provide a dental restoration in which a colour of the dental restoration is controlled. This object is achieved by a method according to claim 19. Advantageously, the arrangement of a dental restoration core with a high intensity colour covered by a translucent veneer layer with a low intensity colour allows to express a resulting colour for the dental restoration composed in a first part by the colour of the core and in a second part by the colour of the veneer layer.

The colour expression is controllable by the thickness of the translucent veneer layer which determines the ratio between the first and the second part.

Advantageously, the colour expression according to the method can provide in a substantially continuous gradient, any colour between the high intensity colour and the low intensity colour since the thickness of the veneer layer can be varied continuously. This allows to have a close match between a dental restoration and the neighboring dental elements of a patient.

BRIEF DESCRIPTION OF THE DRAWINGS

For the purpose of teaching of the invention, preferred embodiments of the method and devices of the invention are described below. It will be appreciated by the person skilled in the art that other alternative and equivalent embodiments of the invention can be conceived and reduced to practice without departing form the true spirit of the invention, the scope of the invention being limited only by the appended claims.

DETAILED DESCRIPTION OF EMBODIMENTS

Figure 1:
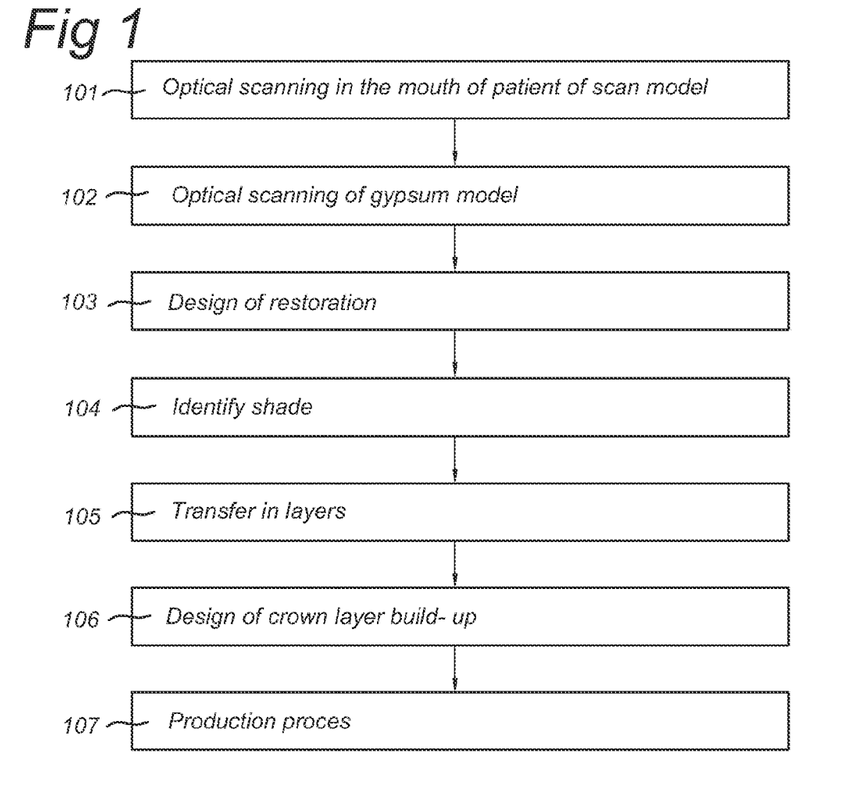
FIG. 1 shows a flow diagram of manufacturing steps for a dental restoration such as an aesthetic crown, abutment, bridge or implant suprastructure.

FIG. 1 shows a flow diagram of manufacturing steps for a dental restoration such as an aesthetic crown, abutment, bridge or implant supra.

In a first step 101, the patient is first diagnosed for a treatment with crowns, abutments, bridges or implant supra-structures. After patient consent at the first visit, the dentist takes an optical measurement directly in the mouth of the patient or makes an impression of the dentures with an impression material on a tray. Next, the impression is cast in gypsum. Then, the dentist takes with another impression material or special bite wax an impression of the antagonists, whereby the patient strongly bites the teeth in a deep, central static occlusion. After complete hardening of the impression material the dentist removes the impression from the mouth of the patient (registration bite). Then in a next step 102, the gypsum impression (cast) is placed in an optical scanner and scanned.

Also in this step 102, the antagonist impression (registration bite) is placed with some seating pressure on the gypsum model, still in the same position in the optical scanner, and the registration bite impression surface is scanned optically (Antagonist Scan).

As a result of the scans, the optical scanner is arranged to provide an image of the gypsum cast.

In a subsequent step 103, the dental restoration is designed in the surrounding of the mouth and in contact with antagonists and any possible neighbor elements. The design of a restoration form follows the following procedural steps: selection of proper element from the library, modeling the restoration on the screen to fit in with the remaining dentition and final adjustment of approximal contacts by the computer. The appropriate tooth elements are chosen by the operator from an extensive collection of generic forms of theoretical teeth in the program's library. When an intact mirror-element can be found in the arch, it can be scanned and used as a standard tooth. The distal and mesial contacts indicated by the operator in the occlusal and buccolingual views of the scan form the first step in the fitting of the generic tooth. The margin line of the new restoration is adjusted to the preparation line that was isolated automatically from the scan of the die.

In a following step 104, the shade (or colour) of the tooth to be replaced is taken by a shade guide or a spectrometric method.

In a next step 105, the dental restoration design is translated into a construction of a layered structure: the core and one or more layers of a veneer glass ceramic.

In a subsequent step 106, a thickness of the glass ceramic layer(s) is determined based on the shade or colour measurements made on the corresponding tooth. A more detailed description will be given below with reference to FIG. 1.

The design of the dental restoration in layers is done, typically allowing for a 10-50 micron cement space between core and veneer glass ceramic.

In connection with the design, the following is noted. By means of a scanner, a rough overall-scan, using steps between consecutive scan lines of 0.2 mm, of the total arch with the preparation is made and converted to a gray-scale Z-chart for use with a computer. In this relief map of the scan, the location of the preparation, the approximal contacts and the extent of the scan area and the neighbouring elements are entered. Within a visual display on the computer, the incisal point, and a cusp tip on the last molar bilaterally can be marked for example, by clicking on the screen using the mouse. From this information the orientation of the occlusal plane in the masticatory system is defined and scanner software (e.g., CYRTINA™) generates a scanning protocol that prevents shadowed parts.

Then, the prepared teeth and the antagonist impression on the model is fine-scanned, using steps between consecutive scan lines of 0,05 mm, with a high definition. After removal from the cast, the cast with the preparation dies are subsequently scanned. A computer generated surface of the prepared tooth is extracted from scan data. The accuracy of the scanning method lies within 0.01 mm.

The design of a restoration form using a CAD/CAM program follows the following procedural steps: selection of proper element from the library, modelling the restoration on the screen to fit in with the remaining dentition and final adjustment of approximal contacts by the computer. The appropriate tooth elements are chosen by the operator from an extensive collection of generic forms of theoretical teeth in the program's library. When an intact mirror-element can be found in the arch, it can be scanned and used as a standard tooth. The distal and mesial contacts indicated by the operator in the occlusal and buccolingual views of the scan form the first step in the fitting of the generic tooth. The margin line of the new restoration is adjusted to the preparation line that was isolated automatically from the scan of the die.

The lingual and buccal boundaries can be selected and dragged with for example the mouse, to shape the restoration so that it fits in a natural appearing row with the adjacent teeth. A warping algorithm generates a deformation field and deformation vectors within the field to generate the new form as directed by the drag vector indicated with the mouse. This way the external contours of the new restoration can be adjusted interactively with the mouse, in much the same way of the building-up of glass ceramic by brush or spatula. After the crown has been fitted into the row, the computer adjusts the mesial and distal contacts to within +/−0.02 mm of the adjacent teeth.

The centric tooth-to-tooth contacts are obtained in relation to the quality of the opposing occlusal surface. Resulting contacts vary from a complex tri-podic occlusal situation in case of an ideal antagonist surface to a simple central contact on a less-defined occlusal surface.

The new restoration is then superimposed on the opposing teeth which are displayed on the screen as a relief map. The CAD/CAM program deforms the generic tooth parametrically (with conservation of shape) according to gnathologic principles. On the library tooth preferred points of contact are used as anchor points to direct the search for contacts with the antagonist. The different fields of contacts of the crown are deformed to give maximal tooth-to-tooth contact with the opposing teeth. Because the theoretical tooth is brought into contact with antagonist as scanned, it can be assumed that contacts are also in the same range as the scanning accuracy that is 0.01 mm.

The occlusal surface should allow cusps to escape and return to their fossae without interferences. Proper prosthetic fabrication should ensure that functional contact relationships are restored for both dynamic and static conditions. Maxillary and mandibular teeth should contact in a harmonious manner that allows optimum function, minimum trauma to the supporting structures, and an even distribution of load throughout the dentition. Positional stability of the teeth is critical if arch integrity and proper function are to be maintained over time.

After the interior and exterior tooth surfaces have been designed, several interface surfaces between cement and ceramic core and between dentine and incisal glass ceramic are defined. The software calculates the interior surface, corrected with marginal gap (0.03 mm), overall cement thickness (0.05-0.10 mm) and ceramic core-die cement thickness (0.02 mm) as specified by the operator. The calculated thickness of the core form and thickness depends on the veneer thickness determined by a color model as discussed in more detail below and by strength considerations. The connectors of a bridge structure are automatically calculated from the place in the mouth and the span of the bridge. Interactive shape corrections by the operator remain possible within the limitations directed by strength considerations.

As indicated by step 107, the dental restoration can now be manufactured according to an embodiment of a manufacturing method of the present invention as described with reference to one of the FIG. 2, 3 or 4.

Figure 2:
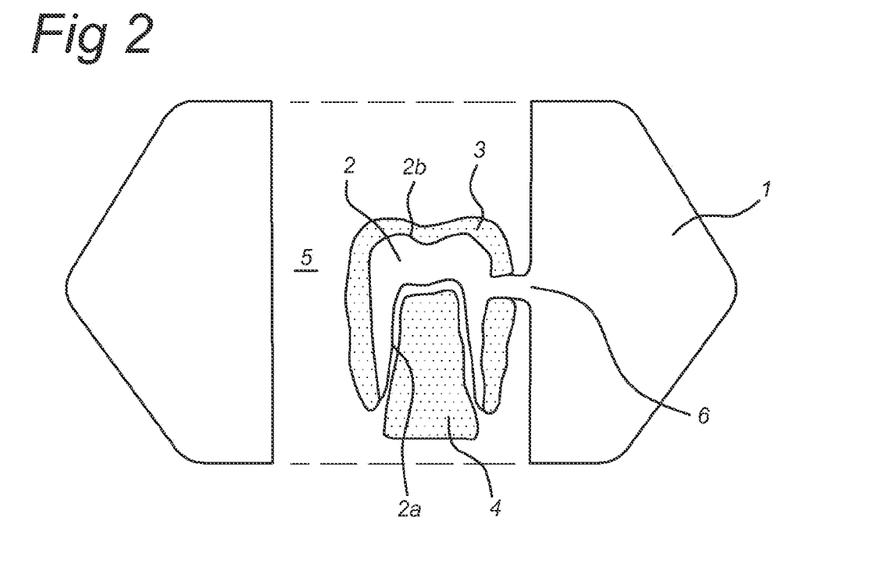
FIG. 2 shows a cross section of a preparation of a dental restoration in an embodiment according to the present invention.

FIG. 2 shows a cross section of a preparation of a dental restoration in an embodiment according to the present invention.

In a block 1 of ceramic material, preferably sintered zirconia or more preferably isostatically pressed yttria stabilized tetragonal zirconia polycrystalline (Y-TZP) zirconia, a dental restoration core 2 is created by a first milling process. The material of the block 1 is cut away to form the dental restoration core 2 within a void 5 inside of the block 1. In the first milling process account taken is taken of a shrinkage due to a later sintering process.

The dental restoration core 2 is fixed within this void 5 by a lingual connector 6 which is arranged to connect the dental restoration core 2 to the remainder of the block 1. The connector 6 is lingual in the sense that the connector is located on a lingual side of the dental restoration.

The milling step for creating the dental restoration core 2, is arranged to create a seat shape 2a of the core 2 that substantially matches a portion of the jaw or a dental stump of a patient, on which the dental restoration core is to be placed. Also, the method is arranged to create an outer shape 2b of the dental restoration core 2, in accordance with the design of the ceramic veneer layer as explained with reference to FIG. 1.

Then, the block is sintered at high temperature e.g., 1450° C. during a suitable time. The material experiences a shrinkage of about 19-25%.

Next, the seat shape 2a of the dental restoration core 2 is sealed by a sealing body 4.

Subsequently, the void 5 within the block 1 is filled with a ceramic slurry for creating the ceramic veneer layer on the outer surface of the dental restoration core 2. The slurry contains a constituent material for forming a veneer layer.

In a following step, the ceramic slurry is then hardened or pre-sintered during a suitable heat treatment to form a veneer layer 3 of the dental restoration. For example, the glass ceramic is pre-sintered at about 600° C. for 1 hour in air until neck forming has taken place to obtain a hardened veneer structure that is stable enough to be handled.

Then, in a second milling step, the hardened ceramic within the void 5 is milled so as to create the ceramic veneer layer 3 on the outer shape 2b of the dental restoration core 2.

Thus, the method for the manufacturing of a dental restoration comprising a dental restoration core 2 and a veneer layer 3, the veneer layer 3 being located at predetermined locations on the dental restoration core 2 and having predetermined thickness at said predetermined locations, comprises
manufacturing the dental restoration core 2;
filling a void 5 in a mould block 1 with a slurry or paste containing a constituent material for a veneer layer, the dental restoration core 2 being positioned in the void 5;
pressing the slurry or paste into the void 5, the void being arranged to have the slurry cover the dental restoration core 2 at least the predetermined locations;
heating the slurry or paste in a hardening or pre-sintering process to obtain a hardened veneer structure covering the dental restoration core 2;
milling a contour of the veneer layer into the hardened veneer structure to form the dental restoration 2, 3.

After the second milling step, the method provides a second thermal treatment of the dental restoration 2, 3 comprising the dental restoration core 2 and the ceramic veneer layer 3. During this second thermal treatment the dental restoration 2, 3 is fully sintered.

During the sintering process some shrinkage of the dental restoration core 2 and the ceramic veneer layer may occur. The shrinkage can be accounted for during the design and the subsequent milling steps.

After the final sintering, the lingual connector 6 is cut to separate the dental restoration 2, 3 from the remainder of the block 1.

The surface of the veneer layer may be polished to remove any remains of the lingual connector 6.

FIGS. 3a-3d show a sectional view of a preparation of a dental restoration in an embodiment according to the present invention.

Figure 3A:
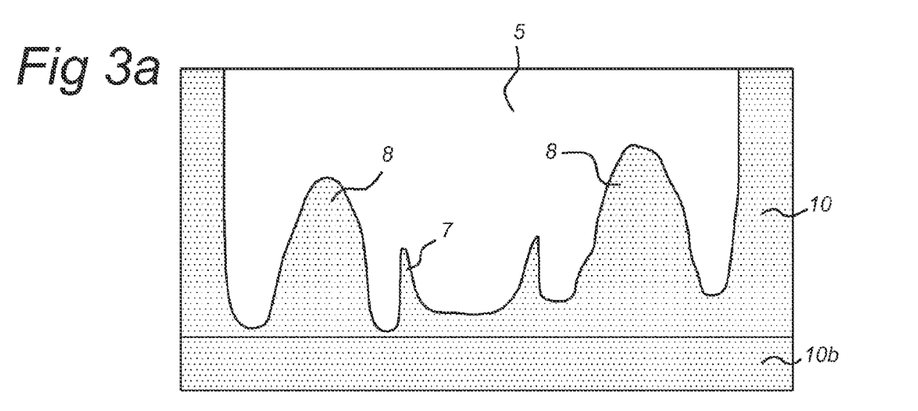
FIGS. 3a-3d show a sectional view of a preparation of a dental restoration in an embodiment according to the present invention.

First, a dental restoration core 2 is created e.g., by milling or a 3D printing process. In this case, the dental restoration core 2 may consist of zirconia or a metal alloy.

Next, in a block 10 a shape contour of a dental restoration core 2 is created by a first milling process. The block 10 may be supported by a carrier 10b. The block 10 is constructed from a material that after manufacturing of the dental restoration can removed without much effort. The material may be one selected from a group comprising gypsum, chamotte, a wax, and a material that can be removed by chemical disintegration.

Within the block 10, a void 5 with surface contour 7 is created by a first milling process, wherein the surface contour comprises replicas of a portion of the jaw or one or more dental stumps 8 of a patient, on which the dental restoration core is to be placed. The first milling process is arranged to produce a surface contour 7 having a contact area of the replicas of the jaw and/or dental stumps that matches a contact area of the dental restoration core 2 when the dental restoration core 2 is positioned on the surface contour 7. Alternatively, a 3D printing technology can be used to create the surface contour 7.

Figure 3B:
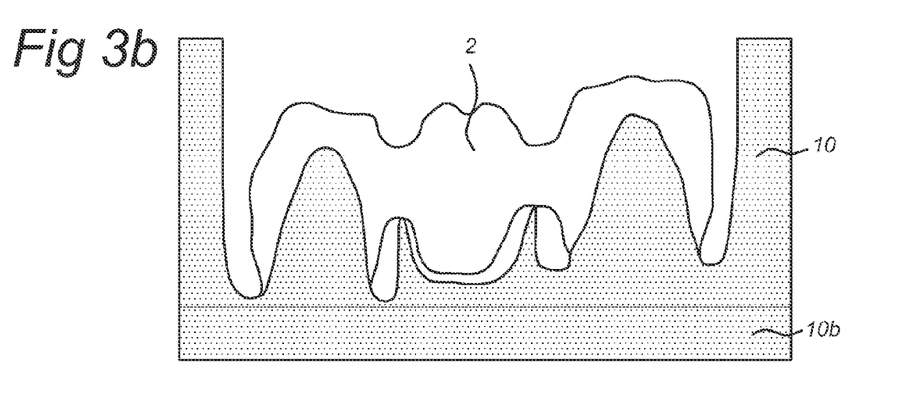

Next, the dental restoration core 2 is mounted on the surface contour 7 of the block 10. FIG. 3b shows the arrangement of block 10 and mounted dental restoration core 2. Above the mounted dental restoration core 2, a void 5 is present in the block 10. Further, the surface contour 7 is arranged with open spaces 11 in areas where a veneer layer is to be created on the dental restoration core 2.

Figure 3C:
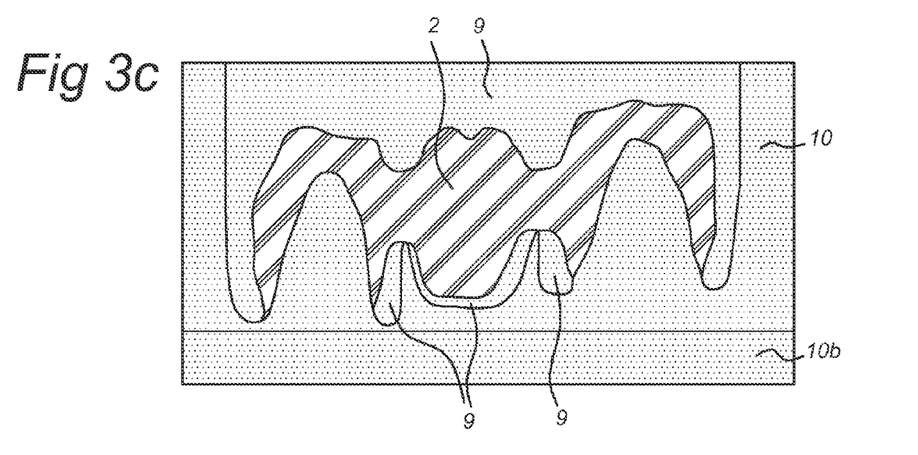

Then as shown in FIG. 3c, the void 5 and open spaces 11 in the block 10 is filled with a slurry of a ceramic veneer material. The ceramic veneer material is a glass ceramic material, for example Sakura™ porcelain. In an example, the slurry may consist of ceramic veneer material mixed with Camphene and a binder.

During filling the slurry is cold pressed to have the ceramic veneer material cover the mounted dental restoration core 2 at the locations of the open spaces 11. Next, the cold pressed ceramic veneer material is hardened for example by a heat treatment to obtain a stable ceramic veneer material 9 suitable for milling.

Figure 3D:
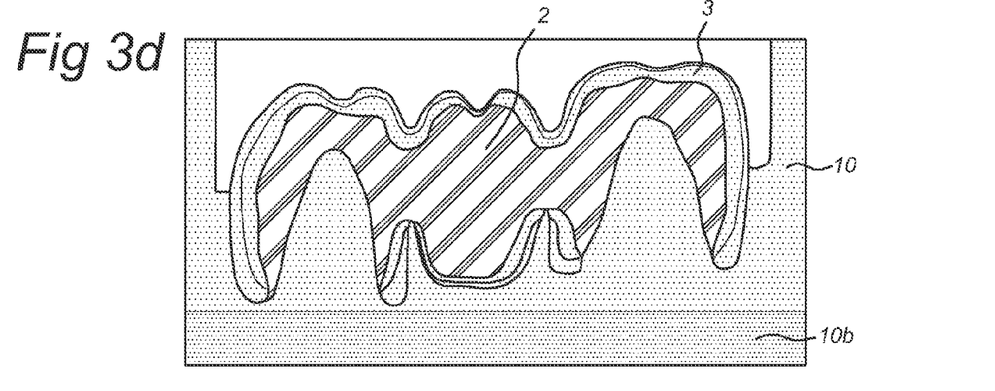

In a next step, as shown in FIG. 3d, the ceramic veneer material 9 is milled in a second milling process to create a veneer layer 3 on the dental restoration core 2.

After the second milling process a further annealing is done to sinter the milled veneer layer 3 so as to enhance the density and the mechanical strength of the veneer layer 3. Sintering may be done at a temperature of about 850° C. for about 2 minutes (which may be different for another ceramic veneer material).

In a further embodiment, after creating the veneer layer 3 the void created by the third milling process may be filled again with a slurry of ceramic veneer material, to create a further veneer layer on top of the veneer layer 3 in a similar way as described above with reference to FIGS. 3c and 3d.

After sintering of the veneer layer(s) the block 10 is broken away or disintegrated in another way to free the dental restoration 2, 3.

Figure 4A:
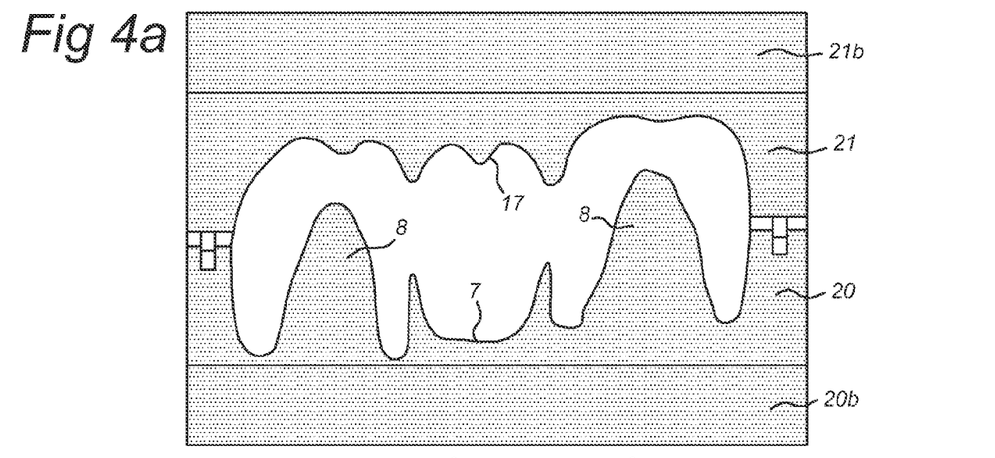
FIGS. 4a-4b show a sectional view of a preparation of a dental restoration in an embodiment according to the present invention.
Figure 4B:
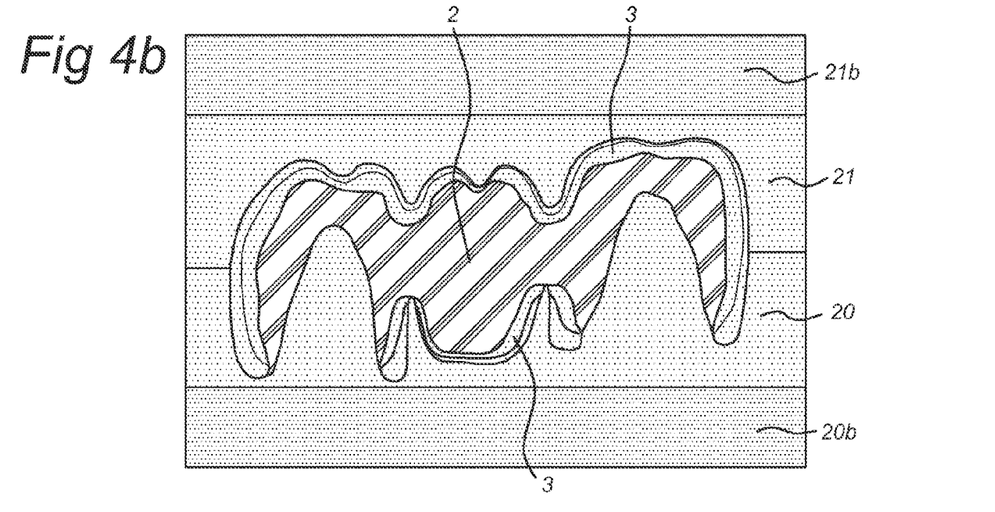

FIGS. 4a-4b show a sectional view of a preparation of a dental restoration in an embodiment according to the present invention.

In this embodiment, in a first step, a dental restoration core 2 is created e.g., by milling or a 3D printing process. In this case, the dental restoration core 2 may consist of zirconia or a metal alloy.

Next, a block 20, 21 is created which comprises a lower mould 20 and an upper mould 21. The lower mould 20 and upper mould 21 are arranged to engage each other and form a compound mould block 20, 21.

The block 20, 21 is constructed from a material that after manufacturing of the dental restoration can removed without much effort. The material may be one selected from a group comprising gypsum, chamotte, a wax, and a material that can be removed by chemical disintegration.

In the lower mould 20, a shape contour of a dental restoration core 2 is created by a first milling process. The lower mould 20 may be supported by a carrier 20b.

Within the lower mould 20, a void 5 with surface contour 7 is created by a first milling process, wherein the surface contour comprises a contact area of replicas of a portion of the jaw and/or one or more dental stumps 8 of a patient, on which the dental restoration core is to be placed. The first milling process is arranged to produce a surface contour 7 to have a match of the dental restoration core 2 and the replicas of the jaw and/or dental stumps. Alternatively the first milling process can be replaced by a first 3D printing process.

In the upper mould 21, a second shape contour 17 is created which substantially corresponds to the surface contour of the veneer layer 3 that is arranged to cover the dental restoration core 2. The second shape contour 17 is created by a further milling process. Alternatively the further milling process can be replaced by a further 3D printing process.

Next, the dental restoration core 2 is mounted on the surface contour 7 of the lower mould 20. Additionally, the upper mould 21 is mounted on the lower mould 20. In this manner, within the block 20, 21 the dental restoration core 2 is mounted on the replicas of the jaw and/or dental stumps, while open spaces 11 exist in areas where a veneer layer is to be created on the dental restoration core 2.

The block 20, 21 comprises a runner (not shown) arranged for guiding a slurry into the block 20, 21.

Then as shown in FIG. 4b, the open spaces 11 in the block 20, 21 is filled with a slurry of a ceramic veneer material. During filling the slurry is pressed to have the ceramic veneer material cover the mounted dental restoration core 2 at the locations of the open spaces 11. Next, the cold pressed ceramic veneer material is hardened or sintered by a heat treatment to obtain a veneer layer 3 on the dental restoration core 2.

After the second milling process a further annealing is done to sinter the milled veneer layer 3 so as to enhance the density and the mechanical strength of the veneer layer 3.

After sintering of the veneer layer(s) the block 20, 21 is broken away to free the dental restoration 2, 3. If needed, the freed dental restoration may be annealed further to enhance the density and the mechanical strength of the veneer layer 3.

It is noted that the method of the present invention can be automated by use of a CAD/CAM system. The CAD/CAM system can be arranged to obtain data of the dental element(s) to be replaced and data of the neighboring elements as well as a portion of the jaw adjacent to the dental element(s) to be replaced or dental stumps on which the dental restoration is to constructed. Further the CAD/CAM system has the capability to design a replacement for the dental element(s) to be replaced and/or to control tools which can carry out the method as described above according to embodiments as shown in FIG. 2-4.

The present invention also relates to a method and system for manufacturing a dental restoration with a controlled shade or colour.

As mentioned above, the prior art predominantly applies shade guides with a number of predetermined shades. A shade for the dental restoration is simply selected by comparing the shade of a tooth or teeth to be replaced with the shades available from the shade guide. Such a comparison is typically done by a visual inspection or in more analytical manner by a shade analyzer. As a result of the fact that in the prior art only discrete shade are available a mismatch between the natural tooth and the replacement tooth may occur.

In the present invention it is however recognized that in human dentition a variety of different colour transparencies of the veneer layer is present. Also, it is observed that natural teeth may have a colour selected from a continuous spectrum (in the visible range) that extends from either reddish or yellowish to white.

The present invention provides a method for manufacturing a dental restoration in which the shade of the replacement tooth is controlled by combining a base colour of the dental restoration core and a surface colour of the veneer layer.

The base colour may differ from the surface colour.

The base colour of the dental restoration core 2 is determined by a pigmentation of the dental restoration core material.

The veneer layer is a glass ceramic having the surface colour, which veneer layer is translucent so as to allow light from the dental restoration core to be transmitted through the veneer layer. The surface colour of the veneer layer 3 may be determined by a pigmentation of the veneer layer material.

The translucency of the veneer layer is controllable by the thickness of the veneer layer. Thus, by varying the thickness of the veneer layer, the amount of light from the base coloured dental restoration core and transmitted through the veneer layer, can be controlled relative to the light directly reflected by the veneer layer.

In an embodiment, the base colour is selected from a reddish colour and a yellowish colour, while the surface colour is a white colour.

In a further embodiment, the base colour may have a high intensity and the surface colour may have a low intensity of the same colour. Such a difference in intensity may be due to a difference in the relative amount of diluting material such as a white pigment. The base colour may have a relatively low amount of white pigment and relatively high amount of reddish (or yellowish) pigment while the surface colour has relatively low amount of reddish (or yellowish) pigment and a relatively high amount of white pigment.

Below, the method for coloring a replacement tooth is explained in more detail.

The colour expression model, presented in this invention, used for determining a colour for a replacement tooth is based on the supposition that the color as appearing to a viewer is obtained from a combination of a surface colour of the glass ceramic or veneer layer as one component and a base colour of the dental restoration core as another component being transmitted through the glass ceramic.

The colour expression is basically governed by the thickness of the veneer layer. The colour as appearing to the viewer is a superposition of the one component from the surface colour and the other component of the base colour. The ratio of the components is determined by the thickness of the veneer layer. The transmission from the base colour decreases with an increase of the thickness of the veneer layer and will finally disappear when the thickness has reached a certain value (optical thickness) where the veneer layer is opaque. At this optical thickness, transmission from the dental restoration core is assumed to be substantially zero. The transmission effect decreases approximately quadratically within the range of interest of the veneer layer thicknesses.

Figure 5:
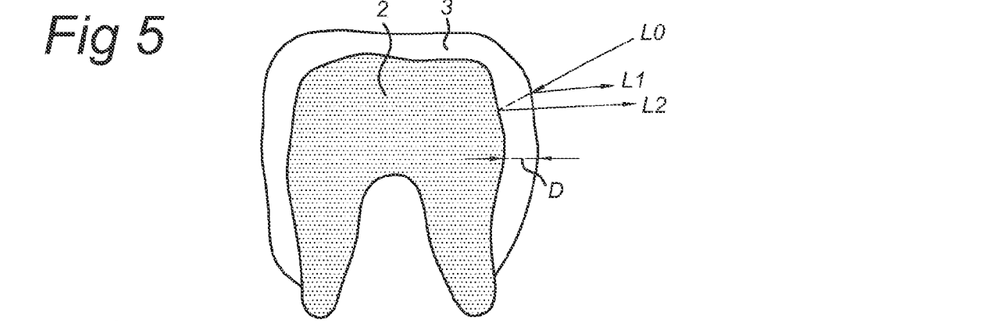
FIG. 5 shows a schematic view of a dental restoration to illustrate the colour expression model according to an embodiment of the present invention.

FIG. 5 shows a schematic view of a dental restoration to illustrate the colour expression model according to an embodiment of the present invention.

The dental restoration shown is a tooth comprising a dental restoration core 2 and a veneer layer 3. The dental restoration core 2 is coloured by the base colour. The colour of the veneer layer which is translucent, is the surface colour.

The colour of the dental restoration is expressed by incident light L0, which partially reflects as indicated by arrow L1 on the veneer layer and which as indicated by arrow L2 is transmitted through the veneer layer, reflects on the dental restoration core 2 and re-transmits through the veneer layer to the ambient.

The perception of the colour of the dental restoration is thus determined by light L1 directly reflected by the veneer layer and by light L2 directed by the dental restoration core under the veneer layer. Due to the base colour in the dental restoration core and the surface colour in the veneer layer, the perceived colour of the dental restoration will comprise a composition of the surface colour and the base colour. The perceived colour will depend on the thickness of the veneer layer, since the thickness of the veneer layer determines the intensity of light reflected by the dental restoration core.

Figure 6A:
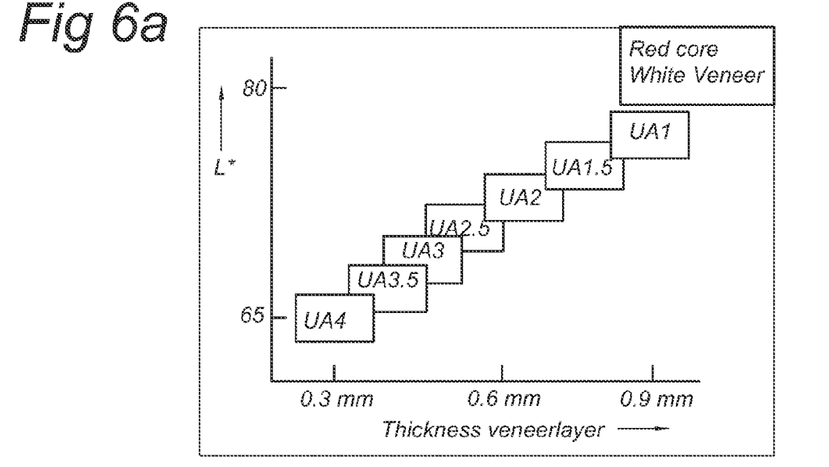
FIGS. 6a-6c show a graphical representation of the dependency of color expressed as L*, a*, b* values in dependence on a thickness of a veneer layer in accordance with an embodiment of the present invention.
Figure 6B:
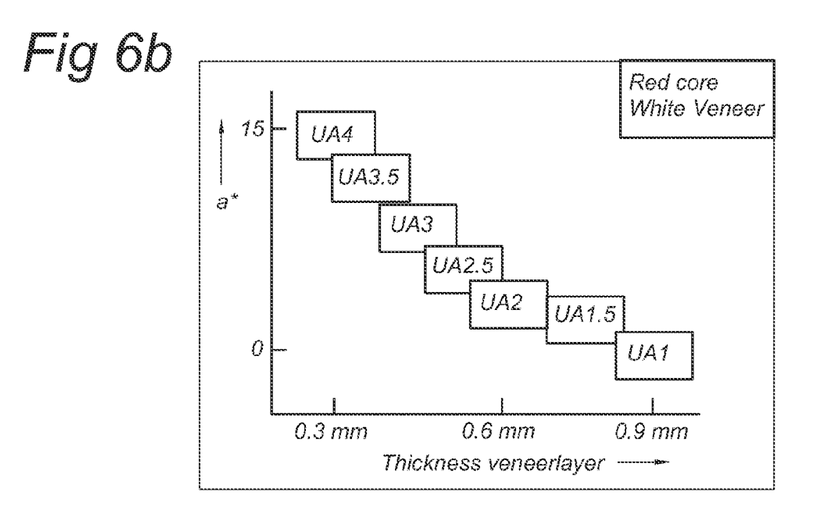
Figure 6C:
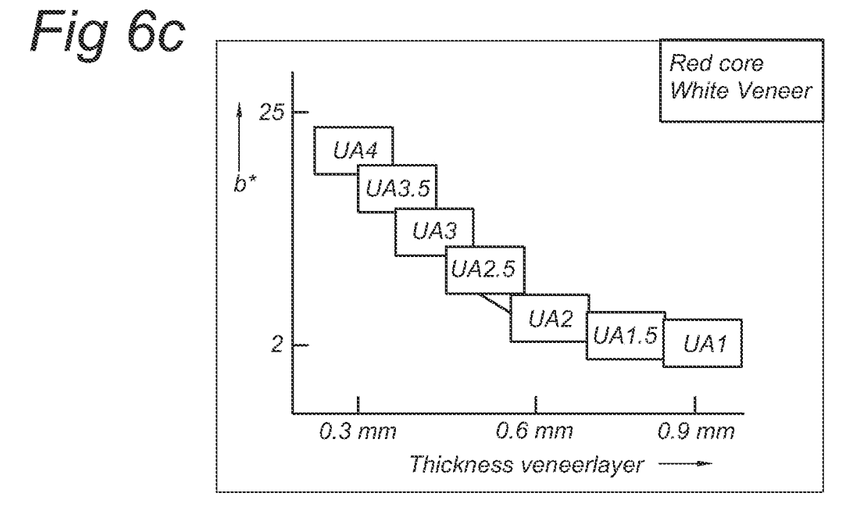

It is noted that due to differences of the veneer layer thickness over the dental restoration, differences in perceived colour can be obtained. FIGS. 6a-6c show a graphical representation of the dependency of color expressed as L*, a*, b* values in dependence on a thickness of a veneer layer in accordance with an embodiment of the present invention.

As will be appreciated by the skilled in the art, L*, a*, b* values relate to the CIE lab colour system.

In these graphs the color expression of the class A shade according to the present invention is shown as a function of the thickness of the veneer layer.

As base colour for the dental restoration core 2, the most reddish shade for a healthy human dentition is chosen. As surface colour for the translucent veneer layer 3, white is chosen.

Within the graphs the color expression is shown in terms of shade codes uA1 . . . uA4. The shade codes uA1 . . . uA4 substantially correspond to the prior art VITA shade guide codes, wherein uA1 is most white and uA4 is most reddish.

Note however that the present invention allows a continuous gradient of colours/shade since in principle the thickness of the veneer layer can be tuned with a desired colour/shade.

The dependency of the colour expression as function of the veneer layer is clearly indicated: the most reddish shade uA4 is obtained for a relatively thin veneer layer while the most white shade uA1 is obtained for a relatively thick veneer layer. A fully white shade is obtained for a veneer layer with a thickness equal or larger than the optical thickness of approximately 2 mm.

Figure 7A:
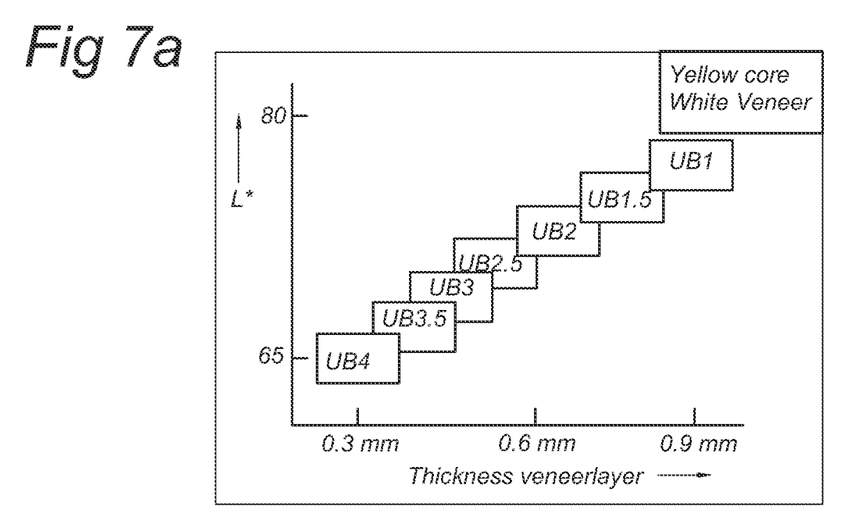
FIGS. 7a-7c show a graphical representation of the dependency of color expressed as L*, a*, b* values in dependence on a thickness of a veneer layer in accordance with an embodiment of the present invention.
Figure 7B:
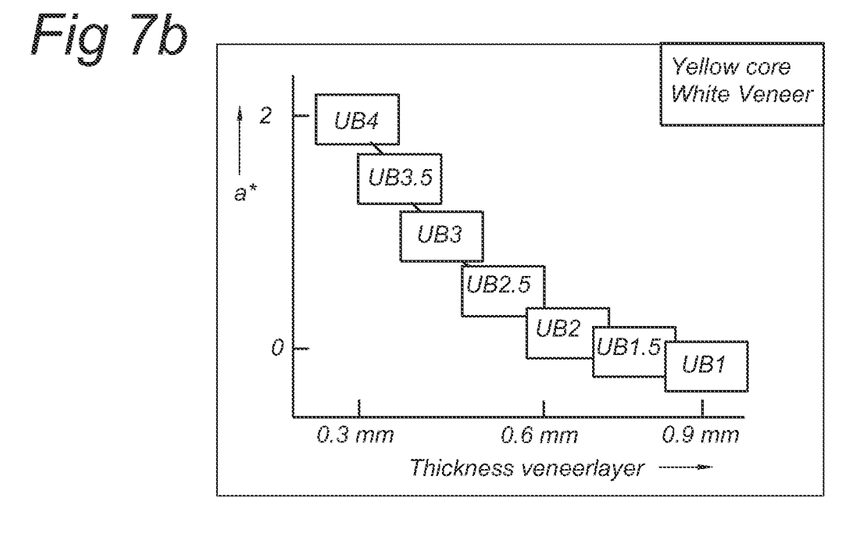
Figure 7C:
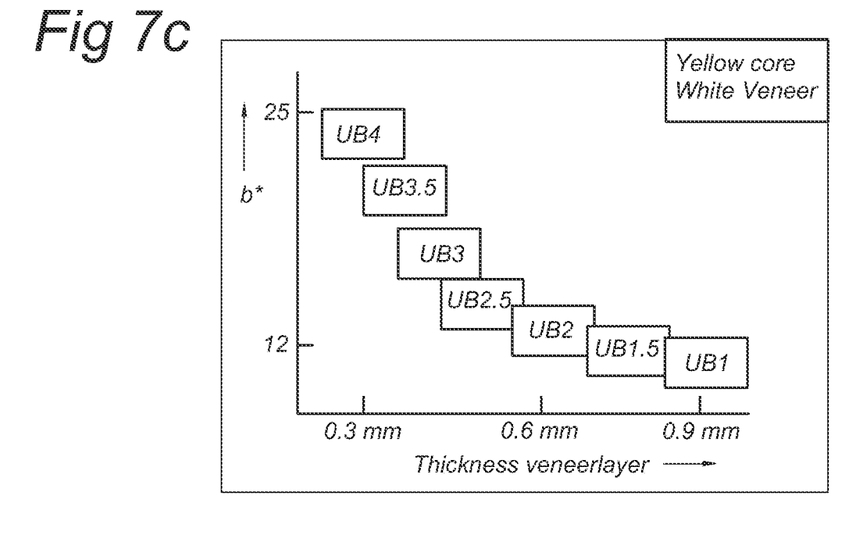

FIGS. 7a-7c show a graphical representation of the dependency of color expressed as L*, a*, b* values in dependence on a thickness of a veneer layer in accordance with an embodiment of the present invention.

In these graphs the color expression of the class B shade according to the present invention is shown as a function of the thickness of the veneer layer.

As base colour for the dental restoration core 2, the most yellowish shade for a healthy human dentition is chosen. As surface colour for the translucent veneer layer 3, white is chosen.

Within the graphs the color expression is shown in terms of shade codes uB1 . . . uB4. The shade codes uB1 . . . uB4 substantially correspond to the prior art VITA shade guide codes, wherein uB1 is most white and uB4 is most yellowish.

The dependency of the colour expression as function of the veneer layer is clearly indicated: the most yellowish shade uB4 is obtained for a relatively thin veneer layer while the most white shade UB1 is obtained for a relatively thick veneer layer. A fully white shade is obtained for a veneer layer with a thickness equal or larger than the optical thickness of approximately 2 mm.

Again, it is noted that the present invention allows a continuous gradient of colours/shade since in principle the thickness of the veneer layer can be tuned with a desired colour/shade.

In a further embodiment, the colour expression may relate to obtain an grey tint for a dental restoration, in which the base colour is a relatively dark grey and the surface colour is relatively light grey or white.

Figure 8:
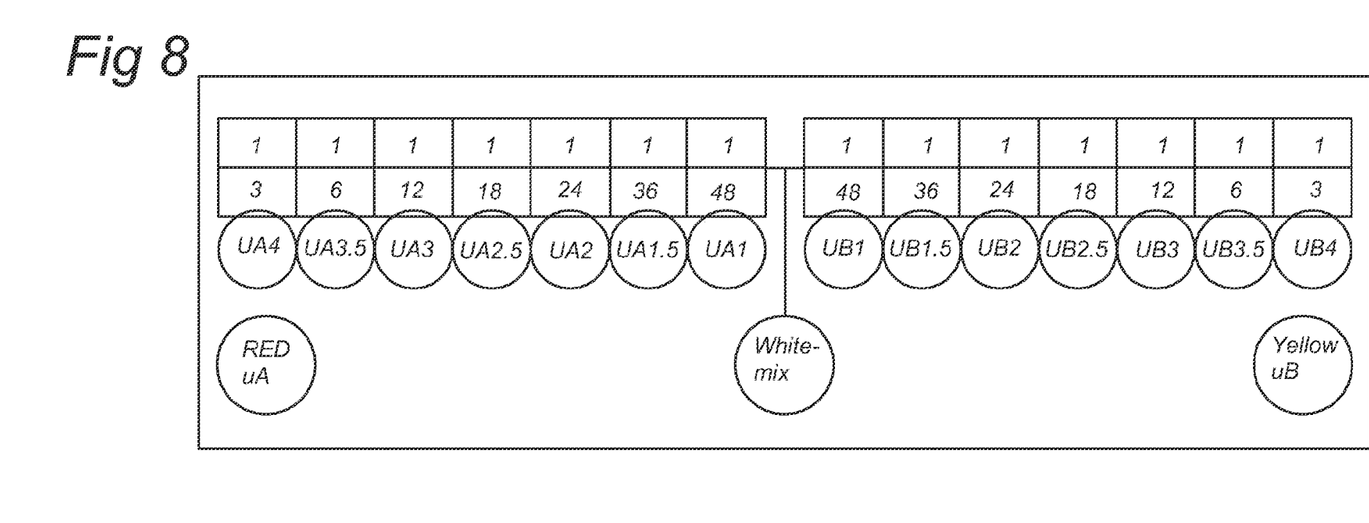
FIG. 8 shows a scheme for a shade guide according to the present invention.

FIG. 8 shows a scheme for a shade guide according to an embodiment of the present invention. In this scheme an example is shown of the mixing relation of the color system and a corresponding shade guide. According to this embodiment, a color or shade of a dental element is obtained by using in the material of the dental element a base colour pigment with high intensity (indicated as uA; uB) and a white pigment component. In principle, any base colour shade with lower base colour intensity can be obtained by mixing the base colour uA; uB with an amount of white pigment. The present invention provides a shade guide of a series of obtainable base colour shades with a shade intensity that is proportional to the ratio of the amount of base colour pigment and the amount of white pigment. In FIG. 8 the series of obtainable base colour shades is shown as a function of the ratio of base colour pigment and white pigment for the class uA (reddish) and the class uB (yellowish).

The mixing ratios of "white" and base colour pigment uA or uB show two similar arithmetical series, whereby the white component is augmented with 50% relative to the amount of the base colour pigment at each step going in the following direction uA4, uA3.5, uA3, uA2.5, uA2, uA1.5, uA1 and uB4, uB3.5, uB3, uB2.5, uB2, uB1.5, uB1. In FIG. 8, the upper line R1 shows the relative portion of the base colour pigment uA; uB. The line R2 shows the relative portion of white pigment (or white mix).

Directly below the line R2, the shade uA4; uA3.5; uA3; uA2.5; uA2; uA1.5; uA1; uB4; uB3.5; uB3; uB2.5; uB2; uB1.5; uB1 that corresponds to a ratio of the relative portion of the base colour and the relative portion of white pigment is shown. As a result in this example seven shades for each base colour are defined by a arithmetical dilution series with a white mix.

In an embodiment, the base colour of a dental core is defined as a mixture of equal amounts of the pigments of the two color groups uA, uB. Then, the composition of a veneer layer to be used on the dental core is provided with a given colour and translucency to obtain any one shade from the series of shades. In this manner, only one core material with a single base colour needs to be used, which reduces the variety of materials needed to manufacture a dental element or tooth sample.

Based on this scheme, testing tooth samples can be manufactured with a particular shade from the shade guide. The shade guide is fabricated from the glass ceramic pigmented in 2× seven steps, to give fourteen colour tabs, for the purpose to provide an easy colour determination of the adjacent dentition of the patient. On these fourteen basic shades the same neutral transparency is applied. In the cervical part the actual body colour must be recognised. Towards incisal a natural dilution of the body colour towards the neutral transparency is clearly visible for individual colour determination.

It is noted that in a similar manner a grey scale can be defined for a grey component of a dental element, depending on the individual greyness of teeth of a patient.
A shade guide for grey scale can be embodied by a number of shades for body ceramic with a decreasing L-value (CIElab) comprising:

"Light" shade, with no grey pigmentation and relatively highest L-values;
"Base" shade with a relatively average amount of grey component, with relatively standard L-values;
"Grey" shade with a relatively higher amount of grey component, with the relatively lowest L-values.

Alternatively the shade guide for grey scale can be embodied by a number of grey shades for the core material and a "Light" shade for veneer ceramic comprising:
"Light" shade core material without grey and the relatively highest L-value;
"Base" shade core material with a relatively average amount of grey component and relatively average L-value;
"Grey" shade core material with a relatively higher amount of grey component, with the relatively lowest L-value.

Figure 9A:
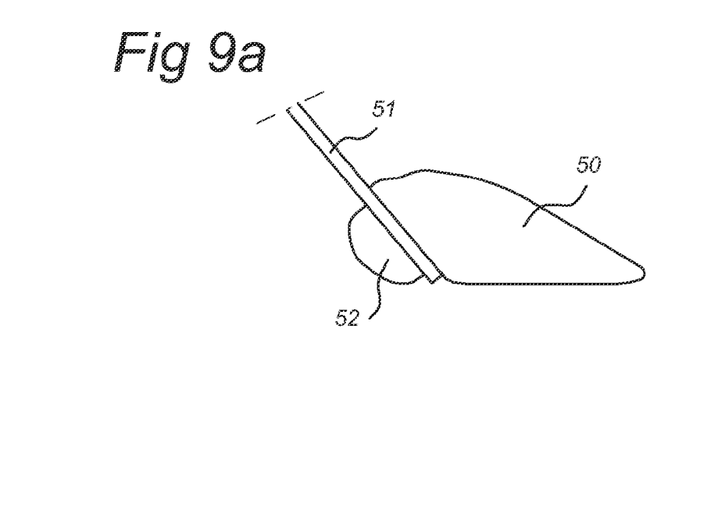
FIG. 9a, 9b show a view of a tooth sample consisting of a dentinal and an incisal layer used with a shade guide according to the present invention and the prior art respectively.

FIG. 9a shows a view of a testing tooth sample 50 consisting of a tooth body with a dentinal and an incisal layer used for a shade guide according to the present invention.

To establish a colour of a patient's dentition a visual inspection can be done by locating a testing tooth sample with a specified colour/shade near a tooth to be replaced and/or next to the neighboring teeth and subsequently comparing the shade of the dentition with the tooth sample. By repeating this procedure with testing tooth samples of various colour/shade, a best match can be established.

The testing tooth sample 50 is fixed to a steel holder strip 51. The steel holder strip 51 is arranged as a grip to the tooth sample 50 at a base end of the tooth by a fixture 52. The strip is oriented relative to the fixture 52 in a direction away from a position of the tooth body relative to the fixture.

Figure 9B:
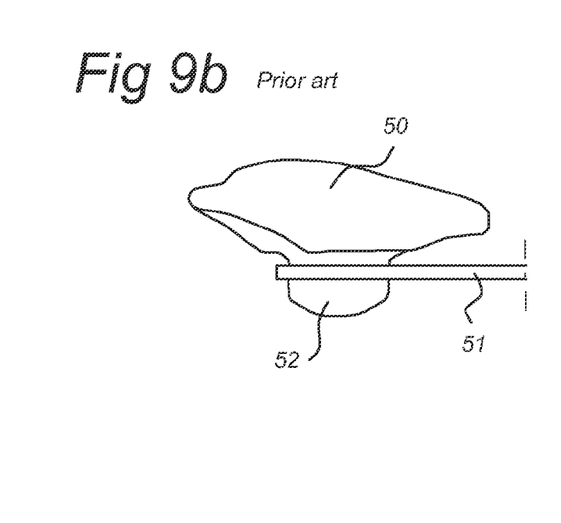

From the prior art (see FIG. 9b) a testing tooth sample is known in which the strip 51 is parallel to the tooth body 50, extends along the tooth body and may reflect light through the tooth body.

The testing tooth sample 50 according to the present invention shown in FIG. 9a avoids reflections of light from the steel holder strip 51 through the tooth body, that can influence the visual inspection, due to the orientation of the strip away from the position of the tooth body relative to the fixture. The strip holder has an angled connection to prevent interference of the strip in a line of vision.

In an embodiment, the strip holder may be attachable to the testing tooth by a magnetic coupling in the fixture.

Further, the shape of the tooth sample 50 and its attachment 51, 52 are chosen so that there is no interference from the holder for conveniently taking the colour in the patient's mouth.

As an alternative, establishing a colour or shade of a tooth to be replaced can be done by means of measurements by a shade analyzer.

Figure 10:
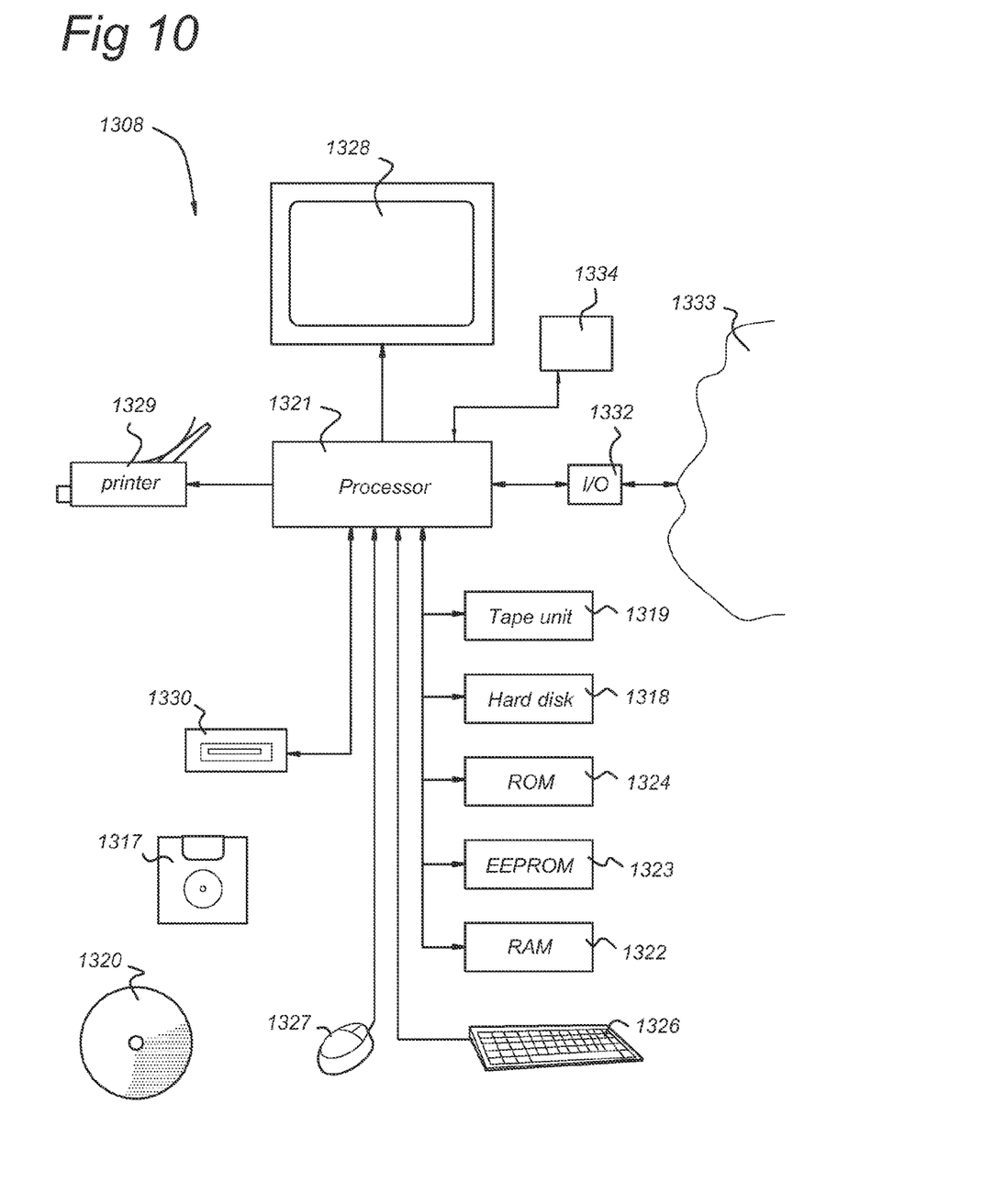
FIG. 10 shows schematically a computer system for use in accordance with the present invention.

FIG. 10 shows schematically a computer system for use in accordance with the present invention.

Computer system 1308 comprises host processor 1321 with peripherals. The host processor 1321 is connected to memory units 1318, 1319, 1322, 1323, 1324 which store instructions and data, one or more reading units 1330 (to read, e.g., floppy disks 1317, CD ROM's 1320, DVD's, a keyboard 1326 and a mouse 1327 as input devices, and as output devices, a monitor 1328 and a printer 1329. Other input devices, like a trackball or a touch screen as well as other output devices may be provided. Further, a network I/O device 1332 is provided for a connection to a network 1333.

Finally, the host processor 1321 is connected to a scanning device 1334 capable of capturing 3D image data from objects. The 3D image data may comprise surface data of the object being scanned. Such an object may be a cast of at least a portion of the dentition of a patient.

The surface data may relate to any measurable property of the object such as colour, roughness, density etc. Also, the host processor is capable of importing data from another computer system by reading data from a data carrier or through the network connection. Such data may be additional data relating to, for example, the dentition of the patient, or for example, a digital library of dental elements.

The memory units shown comprise RAM 1322, (E)EPROM 1323, ROM 1324, tape unit 1319, and hard disk 1318. However, it should be understood that there may be provided more and/or other memory units known to persons skilled in the art. Moreover, one or more of them may be physically located remote from the processor 1321, if required. The processor 1321 is shown as one box, however, it may comprise several processing units functioning in parallel or controlled by one main processor, that may be located remotely from one another, as is known to persons skilled in the art.

The computer system 1308 shown in FIG. 10 is arranged for performing computations in accordance with the method in accordance with the present invention.

Such computations may relate to the design of one or more from the dental restoration system, the dental restoration core 2 and the veneer layer 3.

Alternatively or additionally, the computations may relate to the creation of the block 1; 10; 20, 21 in which the dental restoration is to be shaped.

Alternatively or additionally, the computations may relate to design and/or manufacture a dental restoration with a defined colour or shade in accordance with the colour expression model as described above. Further, the computations may relate to design and/or manufacture a dental restoration with a defined colour or shade in accordance with the arithmetical shade guide as described above with reference to FIG. 8.

Below, some examples are given in relation with embodiments of the present invention.

EXAMPLE 1

First the glass ceramic is transferred into a paste or warm slurry according to the following procedures and materials.

The properties of the materials used in this example are given in table 1.

TABLE 1

| Chemical composition in wt.- %: | Zirconia | Glass ceramic A | Glass ceramic B | Glass ceramic C |
|---|---|---|---|---|
| | | Description | | |
| | Y-TZP zirconia | Silicate ceramic | Silicate ceramic | Silicate ceramic |
| | | Application | | |
| | Structure | Dentin | Incisal | Glaze |
| $SiO_2$ | — | 65 | 65 | 65 |
| $ZrO_2$ | 95 | — | — | — |
| $Al_2O_3$ | — | 16 | 16 | 16 |
| $K_2O$ | — | 9 | 8 | 9 |
| $Na_2O$ | — | 6 | 5 | 10 |
| CaO | — | 1 | 1 | 1 |
| $Ca_3(PO_4)_2$ | — | — | 2 | — |
| $B_2O_3$ | — | 1 | 1 | 2 |
| BaO | — | — | — | 2 |
| $Y_2O_3$ | 5 | 1 | 1 | — |
| $Fe_2O_3$ | 0.1 | 0.5 | 0.5 | — |
| Sinter temperature and hold time in ° C./min. | 1450/60 | 850/2 | 850/2 | 820/2 |

TABLE 1-continued

| Chemical composition in wt.- %: | Zirconia | Glass ceramic A | Glass ceramic B | Glass ceramic C |
|---|---|---|---|---|
| | | Description | | |
| | Y-TZP zirconia | Silicate ceramic | Silicate ceramic | Silicate ceramic |
| | | Application | | |
| | Structure | Dentin | Incisal | Glaze |
| Thermal expansion coefficient in μm/m · K (measured from 25 to 500° C.) | 10.5 | 9.9 | 9.9 | 9.5 |
| Three-point bending strength in MPa | 1000 | 100 | 100 | 80 |

Table 1 shows a zirconia mixed with 1000 ppm representing the core that can be used with dentin veneer shades uA1 to uA4 and uB1 to uB4 (all shades with one core). The core or base color in CIE-lab parameters is given in table 7 as "z2". The glass ceramic is given as example. The most important property of the glass ceramic veneer material is the thermal expansion coefficient, which should not be lower than 90% of the expansion coefficient of the zirconia core material, to keep the weaker glass ceramic component under pressure after cooling down to room temperature. Glass ceramic A is used for the first dentinal layer and glass ceramic B is used for a second opalescent incisal layer.

The glass ceramic veneer component is used as paste (table 2) or as warm slurry (table 3). The preparation is given in the form of a procedure.

TABLE 2

| Component | Description | Composition in wt.- % | | | |
|---|---|---|---|---|---|
| | | Expl. 1 | Expl. 2 | Expl. 3 | Expl. 4 |
| Solid | Glass ceramic | 55 | 55 | 55 | 55 |
| Liquid carrier | De-ionized water | Rest | Rest | Rest | Rest |
| Deflocculant | Dolapix PC64 (Zsimmer & Schwarz) | 0.6 | | | |
| | DarvanC (Vanderbilt) | | 0.7 | | |
| | $AlCl_3$ (pH 8.5 (Ammonia)) | | | 0.8 | |
| | D-3005 (Rohm & Haas) | | | | 1.0 |
| Binder | Methocel a4c (Dow Chemical) | 0.6 | | | |
| | Gelatine | | | 0.6 | |
| Plasticizer | Ethyleneglycol | 1.0 | | | |
| | Glycerine | | | | 1.0 |
| De-foamer | n-octanol | | 0.2 | | 0.2 |
| | Tributylphosphate | 0.2 | | 0.2 | |
| | Byk 023 | 0.05 | 0.05 | 0.05 | 0.05 |

The following procedure describes a possible preparation method for the porcelain paste according to the invention:
1. Weigh and add the solid, plasticizer, dispersant and half the amount of de-ionized water to a ball mill of the proper size for the batch being prepared. The type and size of media are selected based upon the mill size. The media should fill about one-third to one-half of the volume of the mill.
2. Dispersion mill on rollers for 16 to 24 hours at a speed of about 60 rpm.
3. Disperse the binder in rapidly stirring 90° C. in one quarter of the de-ionized water and then add the rest of the water at room temperature water.

4. Add this binder solution to the ball mill and mix for 1 to 2 hours.
5. Pour into another container and slow roll for 24 hours (approximately 1 to 2 rpm) to remove the entrained air.

Camphene porcelain slurry composition in wt.-%

TABLE 3

| Component | Description | Example 1 |
|---|---|---|
| Solids | Glass ceramic | 70% |
| Liquid carrier | Camphene | Rest |
| Defloculant | Hypermer-LP1 | 0.5% |
| Binder | Polystyrene M = 100.000 | 5% |

The following procedure describes a possible preparation method for the porcelain slurry according to this invention:
1. Weigh and add the solid, defloculant and binder to the liquid carrier.
2. Dispersion mill on rollers at 60° C. in an oven with a turning fixture for 16 to 24 hours at a speed of about 60 rpm.
3. The prepared warm slurry is poured in a polyethylene container with a closable drip flute.
4. Let the polyethylene container slow roll for 24 hours (approximately 1 to 2 rpm) in the oven at 60° C. to remove the entrained air.

The restoration is for example produced according to the following procedure, which does not exclude other production methods:
1. Milling or 3D printing a mould surface (a surface contour 7).
2. The milled or 3D printed mould surface in the block is cleaned by compressed air.
3. The inside of the mould is covered with a thin layer of separation material e.g. based on a mixture of high molecular polyethylene glycol in ethanol.
4. The dental restoration core is placed in the correct position on the mould surface and a gentle pressure is applied to ensure proper seating of the core in the block.
5. The block is placed on a vibratory table and the appropriate porcelain paste or slurry is brought into the mould.
6. The block is placed in an hot air oven for about 30 minutes at about 100° C.
7. The top surface of the restoration is milled or 3D printed in the same machine as the inside mould, because of accurate repositioning.
8. The block is heated at about 600° C. without vacuum.
9. The block is removed by breaking away from the presintered restoration.
10. The restoration is fired under vacuum.
11. The porcelain rim around the margin is removed by grinding.

EXAMPLE 2

Examples of pigment composition of the three basic components uA and uB pigment concentrates and white mix of the glass ceramic shades in examples A, B and C are given in table 5.

Table 5 Examples A, B and C pigment compositions of basic components.

TABLE 5

| Pigment, wt % in glass ceramic mixture/ L*a*b*-values | Whitemix | Expl. A | | Expl. B | | Expl. C | | | | | |
|---|---|---|---|---|---|---|---|---|---|---|---|
| | | | | | | "neutral" | | "standard" | | "grey" | |
| | | uA | uB | uA | uB | uA | uB | uA | uB | uA | uB |
| Expl. 1 | | | | | | | | | | | |
| Yellow-ZrV | 0.03 | 0.388 | 0.400 | — | — | — | — | — | — | — | — |
| Brown-SiCrFe | 0.01 | 0.100 | 0.050 | — | — | — | — | — | — | — | — |
| Red ZrSiFe | — | 0.013 | — | — | — | — | — | — | — | — | — |
| Blue-Co$_3$O$_4$ | — | — | 0.025 | — | — | — | — | — | — | — | — |
| White, SnO2 | 0.239 | — | — | — | — | — | — | — | — | — | — |
| L* | 81.1 | 62.42 | 68.35 | | | | | | | | |
| a* | 0.5 | 3.12 | 0.99 | | | | | | | | |
| b* | 11.7 | 25.96 | 27.20 | | | | | | | | |
| Expl. 2 | | | | | | | | | | | |
| Yellow.-ZrVIn | 0.06 | — | — | 0.379 | 0.293 | — | — | — | — | — | — |
| Yellow-SnVTi | 0.04 | — | — | 0.035 | 0.015 | — | — | — | — | — | — |
| Yellow-ZrV | 0.02 | — | — | 0.027 | 0.016 | — | — | — | — | — | — |
| White, SnO$_2$ | 0.239 | — | — | — | — | — | — | — | — | — | — |
| L* | 81.1 | | | 62.42 | 68.35 | | | | | | |
| a* | 0.5 | | | 3.12 | 0.99 | | | | | | |
| b* | 11.7 | | | 25.96 | 27.20 | | | | | | |
| Expl. 3 | | | | | | | | | | | |
| Yellow.-ZrVIn | 0.06 | — | — | — | — | 0.640 | — | 0.640 | — | 0.640 | — |
| Yellow.-SnVTi | 0.04 | — | — | — | — | 0.356 | 0.534 | 0.356 | 0.534 | 0.356 | 0.534 |
| Yellow-ZrV | 0.02 | — | — | — | — | — | 0.472 | — | 0.472 | — | 0.472 |
| Grey, MnO$_2$ | — | — | — | — | — | — | — | 0.01 | 0.01 | 0.02 | 0.02 |
| White, SnO$_2$ | 0.239 | — | — | — | — | — | — | — | — | — | — |
| L* | 81.1 | | | | | 77.9 | 80.5 | 72.9 | 75.5 | 70.9 | 70.5 |
| a* | 0.5 | | | | | 6..2 | 1.5 | 6..2 | 1.5 | 6..2 | 1.5 |
| b* | 11.7 | | | | | 37.6 | 36.4 | 37.6 | 36.4 | 37.6 | 36.4 |

The mixing ratios of "white" and concentrated transparent uA or uB show two similar mathematical series, whereby the white component is augmented with 50% at each step going in the following direction uA4, uA3.5, uA3, uA2.5, uA2, uA1.5, uA1 and uB4, uB3.5, uB3, uB2.5, uB2, uB1.5, uB1.

A second layer in the form of an incisal layer can be applied by repeating the steps described in the procedures. This second transparent incisal cover layer pigment compositions in wt.-% are given in table 6. From iA to iD the grey component is increased, depending on the individual greyness of the teeth of the patient.

TABLE 6

| Pigment, wt % in glass ceramic mixture/ L*a*b*-values | iA | iB | iC | iD |
| --- | --- | --- | --- | --- |
| Yellow. - ZrVIn | 0.06 | 0.06 | 0.06 | 0.06 |
| Yellow - SnVTi | 0.04 | 0.04 | 0.04 | 0.04 |
| Yellow - ZrV | 0.02 | 0.02 | 0.02 | 0.02 |
| Blue, $Co_3O_4$ | 0.01 | 0.01 | 0.01 | 0.01 |
| Grey, $MnO_2$ | 0.01 | 0.02 | 0.03 | 0.04 |
| White, $SnO_2$ | 0.02 | 0.02 | 0.02 | 0.02 |

TABLE 7

| Designation | Description (compositions in weight parts) | Shade in CIE-Lab parameters | | |
| --- | --- | --- | --- | --- |
| | | L* | a* | b* |
| z0 | No pigmentation | 83.90 | −2.04 | −0.14 |
| z1 | 500 ppm $Fe_2O_3$ | 80.14 | −1.36 | 10.19 |
| z2 | 1000 ppm $Fe_2O_3$ | 74.73 | 1.12 | 14.26 |
| z3 | 1500 ppm $Fe_2O_3$ | 70.25 | 3.24 | 16.44 |
| z4 | 1000 ppm $Fe_2O_3$; 20 ppm $MnO_2$ | 72.24 | 1.02 | 13.64 |
| z5 | 1000 ppm $Fe_2O_3$; 40 ppm $MnO_2$ | 69.76 | 3.12 | 15.18 |
| Red core, uA | 0.640 ZrVIn/0.356 SnVTi | 65.02 | 8.32 | 41.40 |
| Yellow core, uB | 0.472 ZrV/0.534 SnVTi | 77.12 | 0.21 | 43.96 |

Table 7 gives the shade in CIE-Lab parameters for differently pigmented zirconia cores.

The tetragonal zirconia compound "3YBCSB" of Tosoh corporation, Tokyo, Japan is pre-mixed with 1000 ppm $Fe_2O_3$ (z2) for pigmentation to a tooth-like shade. The 3-point strength values of zirconia with or without this pigment were similar. The CIE-Lab values as measured with a spectrophotometer are: L* 74.73, a* 1.12 and b* 16.44.

For a system where a grey tinge of the surface color of the veneer is required z4 core with a "Base" shade respectively z5 core with a "Grey" shade can be used.

First the exterior tooth surfaces is designed, including several interface surfaces between the ceramic core and dentine glass ceramic veneer is defined. The CAD-CAM software calculates the interior surface of the top topography of the pigmented zirconia crown. Taking the digital colour of the corresponding tooth the shade type of glass ceramic (uA1 to uB4), which determines the final colour. A hexagon block of isostatically pressed or injection molded 3Y-TZP zirconia was clamped on its two lateral sides in the prismatic clamping device in the milling machine. The crown, abutment, bridge or implant supra structure was milled leaving a connecting bar on the lingual/invisible side of the restoration for keeping the restoration in place during subsequent sintering. The block is given a calibrated indentation for repositioning of the block in the longitudinal direction after sintering. The inside of the copings are blocked with wax.

The block is sintered at 1450° C., and experiences shrinkage of about 19-25%. The block is repositioned in the prismatic clamping device and the longitudinally position measured up by way of optical detection of the calibrated indention that was milled or 3D printed in the previous step in the unsintered block.

Veneering material in a cellulose paste form is applied into the milled space over the crown. After hardening by gel formation at 80° C. in an oven, the top part of the glass ceramic is milled, taking account of the sintering shrinkage of the glass ceramic. The restoration is liberated from the mould and sintered at 850° C. under vacuum to bring the glass ceramic to full density.

The last phase is a glazing step by heating to a temperature that is about 30 degrees under that of the incisal layer (in this example 820° C.).

EXAMPLE 3

The procedure of example 2 is repeated, however the crown is produced with a red core and a white dentine only. The thickness of the veneer layer was kept at 0,6 mm. The shade was found to correspond to uA2.

As will be apparent to one skilled in the art, the colour and translucency map output of an apparatus for measuring the colour of the teeth in the mouth of the patient could be linked to a computer controlled milling or 3D printing apparatus that would mill a layer structure to duplicate the prosthetic device veneering shade according to this map.

This invention is not only concerned with ceramics. The same methods can be used with acrylic composite materials as a cover layer for the crown, abutment, bridge or implant supra structure, bridge or implant supra structure and a zirconia or a metal alloy for the core.

Although the present invention has been described hereinabove by way of preferred embodiments thereof, it can be modified, without departing from the spirit and nature of the subject invention as defined in the appended claims.

The invention claimed is:

1. Method for the manufacturing of a dental restoration by use of CAD/CAM technology, the dental restoration comprising a dental restoration core (2) and a veneer layer (3), the veneer layer (3) being located at predetermined locations on the dental restoration core (2) and having predetermined thickness at said predetermined locations;
the method comprising using the CAD/CAM technology to perform the steps of:
manufacturing the dental restoration core (2), comprising:
milling a mould block (10) to cut away material of the mould block to form a void (5) and the dental restoration core (2) in the void, or milling a block of ceramic material to form a void inside the block (1) and the dental restoration core (2) in the void, wherein the void has a surface contour (7) that has open space (11) in areas where a veneer layer is to be created on the dental restoration core (2);
filling the void (5) with the surface contour in which the dental restoration core (2) is positioned, in the block (1; 10; 20, 21) with a slurry or paste containing a constituent material for a veneer layers
cold pressing the slurry or paste into the void (5), the void being arranged to have the slurry cover the dental restoration core (2) at at least the predetermined locations;
heating the slurry or paste in a hardening or pre-sintering process to obtain a hardened veneer structure covering the dental restoration core (2);

milling a contour of the veneer layer into the hardened veneer structure to form the dental restoration (2, 3); and
sintering the dental restoration.

2. Method according to claim 1, further comprising dimensioning the milled contour of the veneer layer in such a way that a shrinkage during the sintering of the dental restoration (2, 3) is compensated.

3. Method according to claim 1, wherein the dental restoration core is connected (6) by a connector to a remaining part of the milled mould block in the mould block, the connector being formed by the milling process.

4. Method according to claim 3, wherein the block (1) consists of a ceramic material based on zirconia.

5. Method according to claim 3, wherein the block (1) consists of a consumable material wherein the consumable material is selected from a group comprising gypsum, chamotte, a wax, a material that can be removed by chemical disintegration.

6. Method according to claim 1, further comprising creating the void (5) in the block (10) by milling,
wherein the surface contour (7) comprises a replica (8) of a portion of the jaw or one or more dental stumps of a patient, on which the dental restoration core is to be placed.

7. Method according to claim 6, wherein the surface contour (7) has a contact area of the replica (8) of the jaw and/or dental stumps arranged for matching with a contact area of the dental restoration core (2) when the dental restoration core (2) is positioned on the surface contour (7).

8. Method according to claim 1, wherein the block (20, 21) comprises a lower mould (20) and an upper mould (21), the lower mould (20) and upper mould (21) are arranged for forming a compound mould block (20, 21).

9. Method according to claim 8, further comprising:
creating the void (5) in the block (20, 21) by means of:
milling in the lower mould (20) for creating a surface contour 7, wherein the void comprises a surface contour (7) which comprises a replica (8) of a portion of the jaw or one or more dental stumps of a patient, on which the dental restoration core is to be placed,
milling in the upper mould (21) for creating a second surface contour (17) which second surface contour (17) substantially corresponds to a surface contour of the veneer layer (3), and
mounting the upper mould (21) on the lower mould (20).

10. Method according to claim 9, further comprising creating a runner in the block (20, 21), the runner being arranged for guiding the slurry into the block (20, 21).

11. Method according to claim 1, wherein the constituent material for the veneer layer is a glass ceramic or an acrylic composite material.

12. Method according to claim 1, wherein a further veneer layer is arranged on the dental restoration, comprising:
filling a void (5) in a mould block (1; 10; 20, 21) with a slurry or paste containing a constituent material for a further veneer layer, the dental restoration (2, 3) being positioned in the void (5);
pressing the slurry or paste into the void (5), the void being arranged to have the slurry cover the dental restoration (2, 3) at at least the predetermined locations;
heating the slurry or paste in a hardening or pre-sintering process to obtain a hardened further veneer structure covering the dental restoration (2, 3);
milling a contour of the further veneer layer into the hardened further veneer structure.

13. Method according to claim 1, comprising:
providing the material of the dental restoration core (2) with a base colour, providing the constituent material of the veneer layer (3) with a surface colour, wherein the constituent material of the veneer layer is translucent.

14. Method according to claim 13, comprising expressing a colour of the dental restoration (2, 3) by controlling a thickness of the veneer layer (3).

15. Method according to claim 14, wherein the veneer layer (3) has a local thickness between 0.2 and 2.0 mm.

16. Method according to claim 13, wherein the base colour is highly pigmented in either reddish or red-yellow or yellowish and the veneer layer colour is low pigmented in an almost white colour.

* * * * *